United States Patent
Wong et al.

(10) Patent No.: US 9,839,492 B2
(45) Date of Patent: Dec. 12, 2017

(54) ULTRASONIC RING TIP TO ACTIVATE ENDODONTIC INSTRUMENTS

(71) Applicants: Heriberto Bujanda Wong, Hermosillo (MX); Heriberto Bujanda Preciado, Hermosillo (MX)

(72) Inventors: Heriberto Bujanda Wong, Hermosillo (MX); Heriberto Bujanda Preciado, Hermosillo (MX)

( * ) Notice: Subject to any disclaimer, the term of this patent is extended or adjusted under 35 U.S.C. 154(b) by 158 days.

(21) Appl. No.: 14/479,097

(22) Filed: Sep. 5, 2014

(65) Prior Publication Data

US 2015/0064647 A1 Mar. 5, 2015

Related U.S. Application Data

(60) Provisional application No. 62/014,295, filed on Jun. 19, 2014.

(30) Foreign Application Priority Data

Sep. 5, 2013 (MX) .................. MX/u/2013/000473

(51) Int. Cl.
*A61C 1/14* (2006.01)
*A61C 1/07* (2006.01)
*A61C 5/42* (2017.01)

(52) U.S. Cl.
CPC .............. *A61C 1/148* (2013.01); *A61C 1/07* (2013.01); *A61C 5/42* (2017.02)

(58) Field of Classification Search
CPC .......... A61C 1/07; A61C 1/082; A61C 1/148; A61C 5/023; A61C 5/025; A61C 5/026
USPC ...................................................... 433/119
See application file for complete search history.

(56) References Cited

U.S. PATENT DOCUMENTS

| 1,402,229 | A | * | 1/1922 | Hauptmeyer | A61C 5/026 433/102 |
| 2,087,034 | A | * | 7/1937 | Jameson | E21B 31/06 294/65.5 |
| 3,442,000 | A | * | 5/1969 | Dornbos | B21C 23/14 29/417 |
| 3,596,052 | A | * | 7/1971 | Smith | B23K 35/0261 219/138 |
| 3,629,805 | A | * | 12/1971 | Peek | H01R 11/15 23/294 R |
| RE27,339 | E | * | 4/1972 | Dornbos | B21C 23/14 74/586 |

(Continued)

FOREIGN PATENT DOCUMENTS

MX   MX/u/2013000473   11/2013

OTHER PUBLICATIONS

Gary Glassman, DDS & Sam Krachman, DMD., Ultrasonics in Endodontics: Luxury or Necessity?, Sep. 13, 2011, http://www.dentistrytoday.com/endodontic/6067-ultrasonics-in-endodontics-luxury-or-necessity?tmpl=component&print=1&page=.

*Primary Examiner* — Christopher A Flory
(74) *Attorney, Agent, or Firm* — Barbara J. Luther; The Luther Law Firm, PLC

(57) ABSTRACT

A new ultrasonic tip is used to activate endodontic files and includes a tubular body; a ring disposed at one end of the tubular body, the ring having an external diameter and an internal diameter; and the ring having a cut to permit easy insertion of the endodontic file; and a threaded hole at the other end of the tubular body, the threaded hole being capable of screwing onto an ultrasonic hand piece.

11 Claims, 3 Drawing Sheets

(56) References Cited

U.S. PATENT DOCUMENTS

| | | | | |
|---|---|---|---|---|
| 3,721,134 | A * | 3/1973 | Lamke | F16C 7/026 74/586 |
| 3,798,412 | A * | 3/1974 | Smith | B23K 35/0261 219/136 |
| 4,229,168 | A * | 10/1980 | Scholz, Jr. | A61C 1/07 433/102 |
| 4,295,827 | A * | 10/1981 | Martin | A61C 3/03 433/119 |
| 4,425,678 | A * | 1/1984 | Pepper | A22B 5/06 294/74 |
| 4,571,183 | A * | 2/1986 | Nash | A61B 17/1624 433/116 |
| 4,911,639 | A * | 3/1990 | Jacklich | A61C 5/02 433/102 |
| 5,183,360 | A * | 2/1993 | Freeman | B66C 1/66 294/82.1 |
| 5,220,977 | A * | 6/1993 | Wolner | A62B 35/0037 182/18 |
| 5,431,510 | A * | 7/1995 | Reinert, Sr. | B64F 1/20 404/26 |
| 5,474,551 | A * | 12/1995 | Finn | A61B 17/7041 606/264 |
| 5,634,925 | A * | 6/1997 | Urbanski | A61B 17/7037 606/264 |
| 5,643,264 | A * | 7/1997 | Sherman | A61B 17/7037 606/264 |
| 5,752,825 | A * | 5/1998 | Buchanan | A61C 5/023 433/102 |
| 5,863,292 | A * | 1/1999 | Tosic | A61B 17/62 606/56 |
| 5,897,316 | A * | 4/1999 | Buchanan | A61C 5/023 433/102 |
| 5,899,693 | A | 5/1999 | Himeno et al. | |
| 5,951,553 | A * | 9/1999 | Betz | A61B 17/7044 606/246 |
| 5,976,133 | A * | 11/1999 | Kraus | A61B 17/171 606/54 |
| 5,989,250 | A * | 11/1999 | Wagner | A61B 17/7038 606/250 |
| 6,019,602 | A * | 2/2000 | Fletcher | A61C 3/14 433/130 |
| 6,074,391 | A * | 6/2000 | Metz-Stavenhagen | A61B 17/7032 606/278 |
| 6,287,308 | B1 * | 9/2001 | Betz | A61B 17/8095 606/246 |
| 6,309,552 | B1 * | 10/2001 | Hobson, Jr. | B01D 29/15 210/232 |
| 6,416,515 | B1 * | 7/2002 | Wagner | A61B 17/7034 606/250 |
| 6,562,040 | B1 * | 5/2003 | Wagner | A61B 17/7034 606/264 |
| 6,619,957 | B1 | 9/2003 | Mosch et al. | |
| 6,899,715 | B1 * | 5/2005 | Beaty | A61B 17/1604 606/80 |
| 6,976,844 | B2 * | 12/2005 | Hickok | A61C 1/07 433/119 |
| RE39,035 | E * | 3/2006 | Finn | A61B 17/7041 606/264 |
| 7,021,935 | B2 * | 4/2006 | Aeby | A61C 5/026 433/165 |
| 7,080,981 | B2 * | 7/2006 | Terauchi | A61C 5/026 433/141 |
| 7,104,794 | B2 * | 9/2006 | Levy | A61C 1/07 433/119 |
| 7,159,494 | B2 | 1/2007 | Jamnia et al. | |
| 7,367,804 | B2 * | 5/2008 | Lewis | A61C 5/026 433/127 |
| 7,614,878 | B2 | 11/2009 | Paschke et al. | |
| 8,029,543 | B2 * | 10/2011 | Young | A61B 17/7052 606/252 |
| 8,056,445 | B2 * | 11/2011 | Jackson, III | B25B 13/5091 81/487 |
| 2001/0029375 | A1 * | 10/2001 | Betz | A61B 17/8095 606/279 |
| 2002/0026193 | A1 * | 2/2002 | Barker | A61B 17/7037 606/328 |
| 2003/0062726 | A1 * | 4/2003 | Corbett | E05C 19/10 292/101 |
| 2003/0099917 | A1 * | 5/2003 | Wietecha | A61C 3/03 433/119 |
| 2003/0124485 | A1 * | 7/2003 | Teraushi | A61C 5/026 433/141 |
| 2004/0093030 | A1 * | 5/2004 | Cox | A61B 17/0401 606/232 |
| 2004/0126735 | A1 * | 7/2004 | Hickok | A61C 1/07 433/119 |
| 2004/0142302 | A1 * | 7/2004 | Aeby | A61C 5/026 433/141 |
| 2004/0158244 | A1 * | 8/2004 | Clark | A61F 2/0805 606/60 |
| 2006/0068361 | A1 * | 3/2006 | Bergler | A61C 17/20 433/86 |
| 2006/0116677 | A1 * | 6/2006 | Burd | A61B 17/7032 74/1 R |
| 2006/0116687 | A1 * | 6/2006 | Miller | A61B 17/7034 606/270 |
| 2006/0234185 | A1 * | 10/2006 | Ziemba | A61C 1/088 433/119 |
| 2007/0065773 | A1 * | 3/2007 | Hickok | A61C 5/026 433/119 |
| 2007/0270839 | A1 * | 11/2007 | Jeon | A61B 17/7032 606/328 |
| 2008/0096163 | A1 * | 4/2008 | Buchanan | A61C 17/20 433/119 |
| 2008/0319477 | A1 * | 12/2008 | Justis | A61B 17/7089 606/232 |
| 2009/0056476 | A1 * | 3/2009 | Glass | G01L 5/103 73/862.391 |
| 2009/0098507 | A1 * | 4/2009 | Kirstgen | A61C 1/07 433/119 |
| 2010/0139459 | A1 * | 6/2010 | Jackson | B25B 13/5091 81/177.2 |
| 2011/0125192 | A1 * | 5/2011 | Justis | A61B 17/7089 606/279 |
| 2011/0229848 | A1 * | 9/2011 | Hertz | A61C 3/03 433/119 |
| 2011/0282388 | A1 * | 11/2011 | Young | A61B 17/7052 606/252 |
| 2012/0308956 | A1 * | 12/2012 | DeVengencie | A61C 17/20 433/86 |
| 2013/0040263 | A1 * | 2/2013 | Lesage | A61C 3/03 433/119 |
| 2013/0059700 | A1 * | 3/2013 | Gilman | A63B 21/04 482/93 |
| 2014/0107717 | A1 * | 4/2014 | Justis | A61B 17/7089 606/86 R |
| 2015/0012043 | A1 * | 1/2015 | Kumar | A61B 17/7032 606/278 |
| 2015/0102181 | A1 * | 4/2015 | Hook | F16B 45/00 248/68.1 |

\* cited by examiner

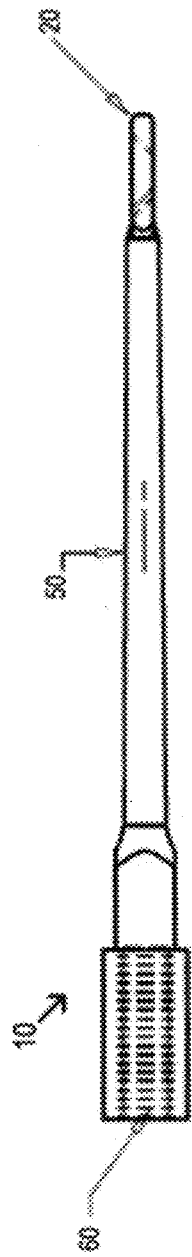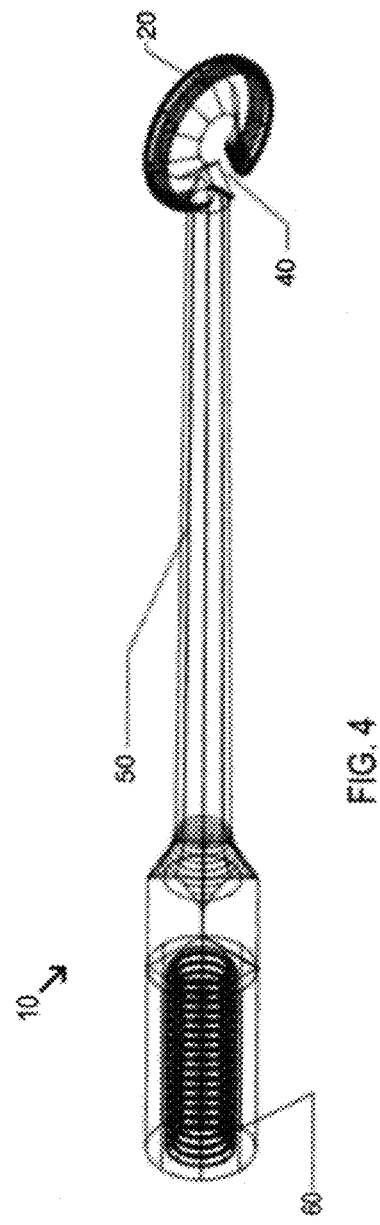

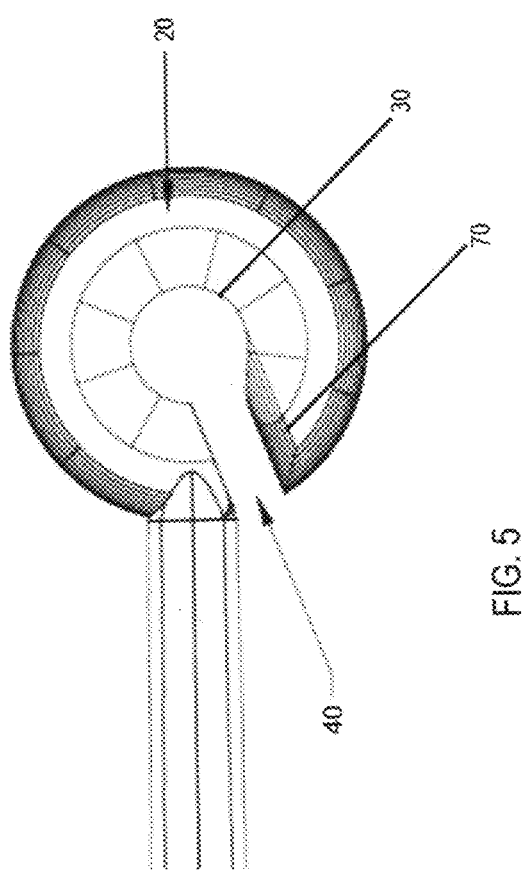
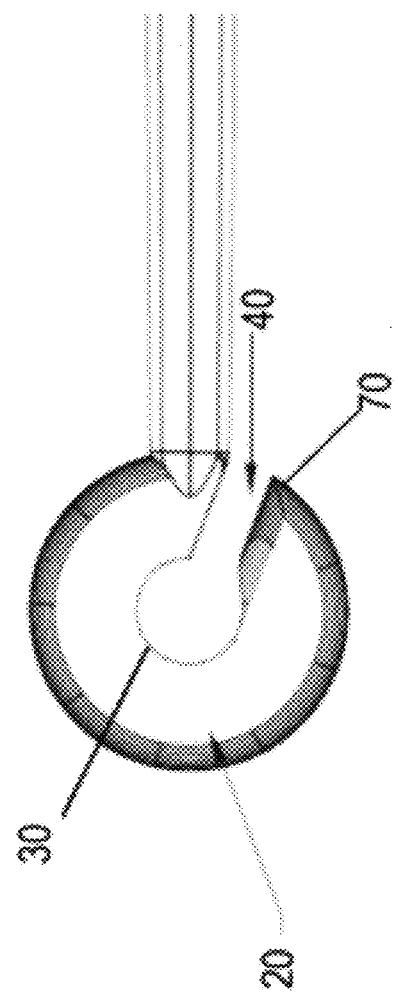
FIG. 5
FIG. 6

ULTRASONIC RING TIP TO ACTIVATE ENDODONTIC INSTRUMENTS

RELATED APPLICATIONS

This application claims the benefit of U.S. Provisional Application No. 62/014,295 filed Jun. 19, 2014. This application is a continuation in part of Mexican Utility Model No. MX/u/2013/000473 filed Sep. 5, 2013. The prior patent applications are hereby incorporated by reference.

TECHNICAL FIELD

This invention generally relates to dental instruments and more specifically to an ultrasonically energized apparatus for more effectively operating endodontic instruments in performing root canal treatments.

BACKGROUND

Files and other ultrasonic instruments are used to remove the tooth pulp as well as to clean, shape and disinfect inside the root canals during endodontic treatments. Importantly root canals are very small in length as well as in caliber. Thus, a high degree of tactile perception and control is required during the endodontic treatment. As part of the procedure, the operator first obtains an image of the inside of the problem tooth. This shows whether the root canal is straight or crooked, is unobstructed or obliterated, has side channels or is calcified. The image can also be used to approximate the depth of the root canal. For an exact depth, the apex locator utilizing electrical resistance of tooth tissues is used. A working distance indicator, or "stop," is attached to the file or other instrument to mark the apex distance and operatory limit.

There are in the market ultrasonic systems with hand pieces onto which ultrasonic instruments are fastened. In many circumstances, these ultrasonic instruments have replaced the inexpensive endodontic files used without benefit of ultrasound. These ultrasonic instruments are fastened to the ultrasonic hand piece in a similar way to how a drill bit is fitted to an electric drill.

The current ultrasonic system has two drawbacks: First, it delays the procedure while the operator unfastens one instrument and fastens another to the hand piece. Second, the operator experiences poorer tactile perception and control of the instrument, as compared to operating light-weight files by hand.

The above described ultrasonic systems have been shown to create accidental perforations, ledges, "transport of the apical region," files fractures, over enlargement of the canals and other procedural errors. Despite their advantages, these factors have caused experts to stop recommending ultrasound use for the canal preparation. Currently, these ultrasonic systems are mostly used to help in the disinfection process of the treatment. The operator removes tissue and shapes the canal manually or mechanically with files (without ultrasound) and frequently switches to ultrasonic disinfection with fluid and then back to the other process.

SUMMARY

In one embodiment, an ultrasonic tip is used to activate at least one endodontic file. The new tip has a tubular body with a ring and a threaded hole. The ring is disposed at one end of the tubular body and has an external diameter and internal diameters. The internal diameters are at least an upper and a lower internal diameter, with the upper internal diameter exceeding the lower internal diameter. The internal diameter optionally tapers from the larger upper internal diameter to the lower internal diameter. The ring also has a cut to permit easy insertion of the endodontic file. The threaded hole at the other end of the tubular body is capable of screwing onto an ultrasonic hand piece, whereby the cut permits the sideways insertion of the endodontic file into the ring without disturbing a working length indicator.

Optionally, the ultrasonic tip material of the tip is stainless steel, titanium or nickel titanium. Alternatively, the tubular body has a configuration to provide strength and light weight. The ultrasonic tip's cut width slightly exceeds the width of a standard file, as do the upper and lower internal diameters of the ring.

In another embodiment, an ultrasonic tip used to activate at least one endodontic file and has a tubular body with a ring and a threaded hole. The ring is disposed at one end of the tubular body and has an external diameter and an internal diameter. The ring also has a cut to permit easy insertion of the endodontic file. The other end of the tubular body has a threaded hole at the other end of the tubular body, and the threaded hole is capable of screwing onto an ultrasonic hand piece, whereby the cut permits the sideways insertion of the file into the ring without disturbing a working length indicator.

Optionally, the ultrasonic tip material of the tip is stainless steel, titanium or nickel titanium. Alternatively, the tubular body has a configuration to provide strength and light weight. The ultrasonic tip's cut width slightly exceeds the width of a standard file, as does the internal diameter of the ring. The ultrasonic tip's cut and internal ring diameter accommodate other endodontic instruments, including but not limited to explorers, scalps, endodontic burs, spoon excavators and Gates Glidden drills.

BRIEF DESCRIPTION OF DRAWINGS

FIG. 3 is a lateral view of the same embodiment of the invention, where it can be appreciated that the rest of the invention viewed from the side looks the same as viewing it from above or from below, except for the part of the ring.

FIG. 4 is a perspective view of the same embodiment of the invention where all the components can be appreciated: threaded hole, for the tip to be connected to the ultrasonic equipment; tubular body and ring tip with a cut, where it can be appreciated that the lateral part of the ring is rounded.

FIG. 5 is a detailed overview of one embodiment of the ring, where it is shown that the internal diameter at the bottom is smaller than the internal diameter of the top.

FIG. 6 is a view from below the same ring, where the internal diameter at the bottom is shown and the external diameter of the ring is visible and is the same for the top and the bottom.

DETAILED DESCRIPTION

I have been an endodontist for 30 years and have used ultrasonic tools in root canals for 20 years. I have given talks about the best ways to perform this type of surgery. While I have seen many improvements, we are still looking for procedures that provide ultrasound advantages with the levels of control and precision that the manual techniques provide. With my invention we provide the advantages of ultrasound (like excellent disinfection) while avoiding the disadvantages due to reduced tactile sensation and control. Now in one efficient procedure, we provide the advantages of simultaneous and continuous disinfection combined in one instrument with increased efficiency and eliminating risks mentioned above.

Particularly to those of us used to being able to precisely manipulate a non-ultrasonic file, the current ultrasound apparatus diminishes the tactile feel from the file and control. In addition, current instruments require the surgeon to screw or otherwise secure the file directly to the ultrasonic hand piece. This takes time. The file needs to be uncoupled or unscrewed before we can replace the file with either a new one or a different size.

Moreover, the "instruments" sold with ultrasonic hand pieces have been upgraded for attachment and are several times more expensive than the simple files used with manual techniques. I experimented with new configurations that would solve these problems of awkwardness, decreased sensitivity, inefficiency and cost.

My new ultrasonic tip not only accommodates and activates common files, it also can activate other instruments including but not limited to explorers, scalps, spoon excavators, gate gliders, drills and endodontic burs. In addition, my invention enables cleaning, shaping and disinfecting at the same time. Because of better tactile feel and control, I minimize files bending and fracturing for additional patient safety, surgeon efficiency and cost reduction.

Figure 1:
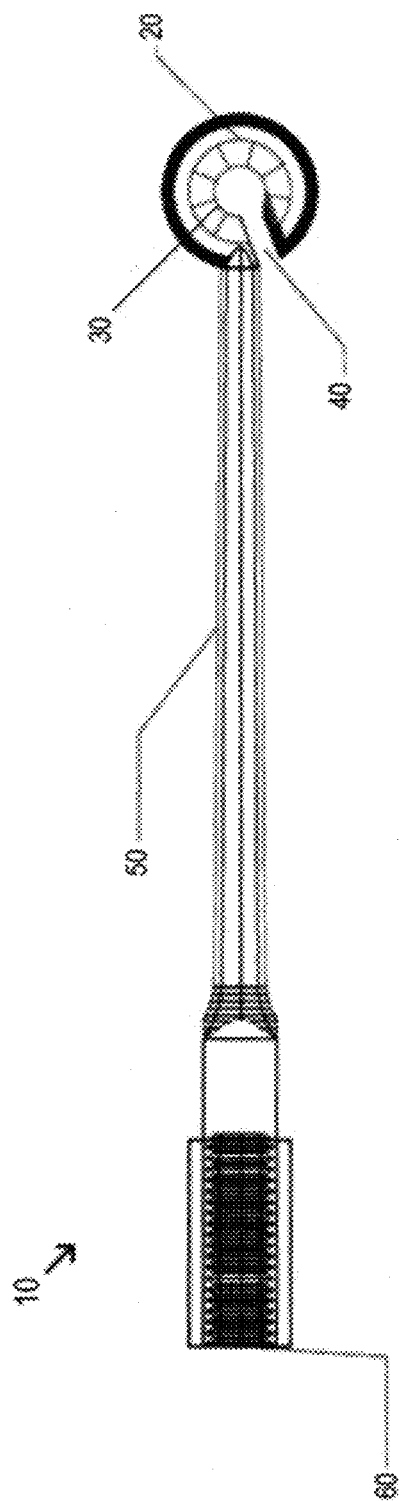
FIG. 1 is a top view of one embodiment of the invention, where all the components can be appreciated. It shows the characteristics of the ring and the cut viewed from above.

Starting with FIG. 1, a top view of one embodiment of the inventive ultrasound tip shows all the component parts. It shows the characteristics of the ring and the cut viewed from above. The invention is a new ultrasonic tip 10, preferably made of stainless steel. At one end of the tip 10, there is a ring 20 with varying internal diameters. The internal diameter at the bottom 30 is smaller than the internal diameter of the top but larger than the caliber of the fines being used (not shown). The external diameter of the ring 20 is the same for the top and the bottom. The outer, lateral surface of the ring may be rounded to give it a donut shape.

While the ultrasonic tip is shown with a circular ring, it should be understood that the file can be ultrasonically activated with any shape of the tip where the ring 20 is shown. The inside and outside of the activated tip can be the same or different shapes. Preferably the internal surface of the "ring" is curved including oval. More preferred is a circular internal ring. The curved internal surface enables the operator to smoothly slide the file into position. Pressing the file against the internal side helps the operator direct the file into any working area and away from danger zones.

The ring has a cut 40 in one side that allows fines (not shown) to be slipped/placed inside the ring sideways. Importantly this design allows fines to be inserted inside the ring without the need of removing the stop thus increasing safety. On the other end of the tubular body 50 of the ultrasonic tip 10, there is a threaded hole 60 for the ultrasonic tip 10 to be connected to the ultrasonic hand piece (not shown). In this way, the invention allows the operator to manipulate an inexpensive file by hand with no loss of tactile perception or control and at the same time allows the file to be activated ultrasonically because the hand-held file directly contacts the inside surface of the ring. The ring shape of the tip, allows the operator to direct the file laterally from a wide range of angles in order to move the file to the correct working area at the right angle.

At least the shaft and the ring of the invention—as well as any contact with the ultrasonic energy source—must be made of a hard material for most effective ultrasonic energy transmission. Hard materials enjoying use in ultrasonic dental practice include, but are not limited to, stainless steel, titanium and nickel titanium. The preferred material is stainless steel. Most currently available plastics are not preferred because they damp the ultrasonic waves.

Figure 2:
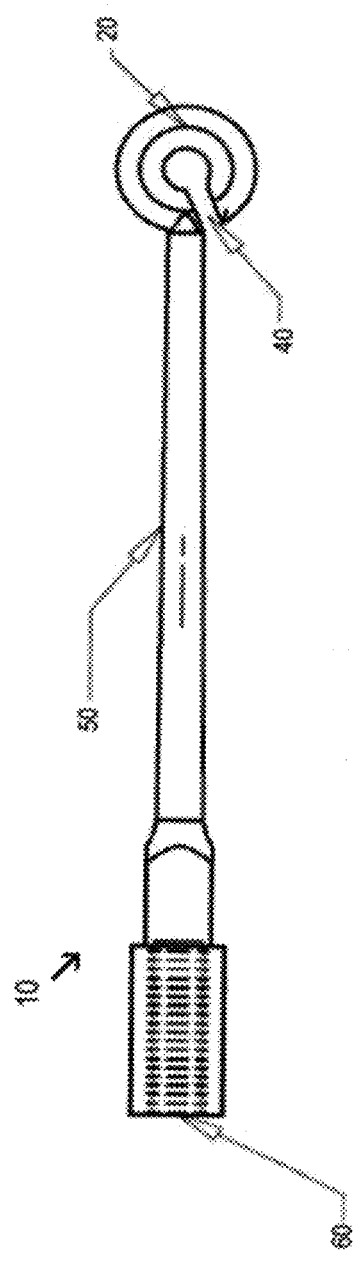
FIG. 2 is a view from below of the same embodiment.

Turning now to FIG. 2, the ultrasonic tip 10 looks like FIG. 1, except for the different view of the ring 20. Here the flat bottom of the ring is more visible with internal diameter 30.

Turning now to FIG. 3, the ultrasonic tip 10 is pictured from the side and looks like FIGS. 1 and 2, except for the profile of the ring 20. The tapered internal portion of the ring 20 permits the operator to turn and slant the file manipulated within the ultrasonic tip 10.

Turning now to FIG. 4, the invention is displayed in a perspective view of the top. The ring 20 is shown with its cut 40 for entrance of the file (not shown). Even the lateral surface of the ring 20 is rounded. The perspective view allows a view of the threaded hole 60, which is attached to the ultrasonic hand piece (not shown).

Turning now to FIG. 5, a close-up of the ring is shown. Dotted lines 70 show the internal profile of the ring 20. Here, the inner diameter of the ring 30 is shown, as is the cut 40. One side 70 of the cut 40 is shown in perspective.

Turning now to FIG. 6, the ring 20 with its internal diameter 30 is shown from below. Tapered surface 70 (dotted line) is now visible. In another embodiment, the ring has one internal diameter for top and bottom. In another embodiment, the two internal diameters are not connected with a taper.

Now that the various parts of the new ultrasonic tip 10 have been described, it is easier to appreciate the invention's design and parts significance. The most important functions of the invention are:

First, the ultrasonic tip ring ultrasonically activates the inexpensive files as well as other instruments including but not limited to explorers, scalps, endodontic burs, spoon excavators and Gates Glidden drills upon contact with the internal surface of the ring.

Second, the file easily slips into the ring through the cut so there is no need to remove the working stop indicator as you move from one to different file calibers.

Third, it is not necessary to perform the additional step of immovably fitting or screwing the file to the ultrasonic hand piece.

Fourth, the files activated by the inventive tip are more easily and sensitively maneuvered by hand and are thus able to get inside calcified canals that are partially or totally obliterated as opposed to other techniques that depend on manually or mechanically working the canals that frequently end up with bent files, fractured files (with obstructed canals), ledges and perforated canals.

Fifth, treatment with this new style of ultrasonic tip facilitates precise shaping of the canals as well as the more effective cavitation of disinfection solutions. More effective cavitation loosens and lifts remaining debris from the canal space.

Sixth, the inventive ultrasonic tip aids in the removal of fractured files, even those located in the apical region, by using narrow files and removing less tooth. Finally, during re-treatment procedures, this method of ultrasonic activation of the file aids in removing previously fixed tooth-filling material because the system effectively transfers heat and softens common filling materials, such as gutta-percha.

There are multiple ways to use the invention. Here are two exemplary methods: In the first method, one hand is used to hold the hand piece of the ultrasonic hand piece while the other hand is used to manipulate the file or other instrument. Preferably the file is initially positioned on or adjacent to the working area inside the tooth. Then the upper part of the file is then slipped inside the ring through the side cut. The file is then energized ultrasonically by the contact of the inside wall(s) of the ring. The ultrasonic energy from the ring passes into the file where it causes vibratory movement.

In the second method, the same technique is performed with a single hand. After positioning the file within the tooth and ring, the file is guided by the index finger of the hand supporting the ultrasonic hand piece. With either of these techniques, conventional files are used, which are readily found at low cost in the market.

As for how to make the inventive ultrasonic probe, a preferred method is lathing on a computer numerical control (CNC) machine. Alternative methods of manufacture include but are not limited to molding.

Although specific embodiments have been illustrated and described herein, those of ordinary skill in the art will appreciate that any arrangement calculated to achieve same purposes can be substituted for the specific embodiments shown. This disclosure is intended to cover any and all adaptations or variations of various embodiments of the invention. It is to be understood that the above description has been made in an illustrative fashion, and not a restrictive one. Combinations of the above embodiments, and other embodiments not specifically described herein will be apparent to those of skill in the art upon reviewing the above description. The scope of various embodiments of the invention includes any other applications in which the above structures and methods are used. Therefore, the scope of various embodiments of the invention should be determined with reference to the appended claims, along with the full range of equivalents to which such claims are entitled.

In the foregoing description, if various features are grouped together in a single embodiment for the purpose of streamlining the disclosure, this method of disclosure is not to be interpreted as reflecting an intention that the claimed embodiments of the invention require more features than are expressly recited in each claim. Rather, as the following claims reflect, inventive subject matter lies in less than all features of a single disclosed embodiment. Thus the following claims, and such other claims as may later be added, are hereby incorporated into the description of the embodiments of the invention, with each claim standing on its own as a separate preferred embodiment.

Reference throughout this specification to an "embodiment," an "example" or similar language means that a particular feature, structure, characteristic, or combinations thereof described in connection with the embodiment is included in at least one embodiment of the present invention. Thus appearances of the phrases an "embodiment," and "example," and similar language throughout this specification may, but do not necessarily, all refer to the same embodiment, to different embodiments, or to one or more of the figures. Additionally, reference to the words "embodiment," "example" or the like for two or more features, elements, etc., does not mean that the features are necessarily related, dissimilar, the same, etc.

Each statement of an embodiment or example is to be considered independent of any other statement of an embodiment despite any use of similar or identical language characterizing each embodiment. Therefore, where an embodiment is identified as "another embodiment," the identified embodiment is independent of any other embodiments characterized by the language "another embodiment."

The features, functions and the like described herein are considered to be able to be combined in whole or in part one with another as the claims and/or art may direct, either directly or indirectly, implicitly or explicitly.

As used herein, "comprising," "including," "containing," "is," "are," "characterized by," and grammatical equivalents thereof are inclusive or open-ended terms that do not exclude additional un-recited elements or method steps. "Comprising" is to be interpreted broadly and including the more restrictive terms "consisting of" and "consisting essentially of."

Reference throughout this specification to features, advantages, or similar language does not imply that all of features and advantages that may be realized with the present invention should be or are in any single embodiment of the invention. Rather, language referring to the features and advantages is understood to mean that a specific feature, advantage or characteristic described in connection with an embodiment is included in at least one embodiment of the present invention. Thus, discussion of the features and advantages, and similar language, throughout this specification may, but does not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized and certain embodiments that may not be present in all embodiments of the invention.

The invention claimed is:

1. An ultrasonic tip used to activate at least one endodontic file comprises
   a. a tubular body;
   b. a ring disposed at one end of the tubular body,
      i. the ring having an external diameter and internal diameters;
      ii. the internal diameter comprising at least an upper and a lower internal diameter, with the upper internal diameter exceeding the lower internal diameter and both internal diameters being larger than a caliber of the endodontic file, thus configured to enable angular motion of the endodontic file;
      iii. the internal diameter optionally tapering from the larger upper internal diameter to the lower internal diameter; and
      iv. the ring having a cut sized narrower than the internal diameters, sized to permit easy insertion of the endodontic file and free movement of the file within the ring; and
   c. a threaded hole at the other end of the tubular body, the threaded hole configured to screw onto an ultrasonic hand piece, whereby the cut permits the sideways insertion of the endodontic file into the ring without disturbing a working length indicator, and the ring activates the file upon manual pressure of the file against the ring.

2. The ultrasonic tip of claim 1 wherein the material of the tip comprises stainless steel, titanium or nickel titanium.

3. The ultrasonic tip of claim 1 wherein the cut width slightly exceeds the width of a standard file.

4. The ultrasonic tip of claim 1 wherein the upper and lower internal diameters of the ring exceed the width of a standard file.

5. The ultrasonic tip of claim 1, wherein the ring is sized to accommodate explorers, scalps, endodontic burs, spoon excavators and Gates Glidden drills.

6. An ultrasonic tip used to activate endodontic files comprises
   a. a tubular body;
   b. a ring disposed at one end of the tubular body,
      i. the ring having an external diameter and an internal diameter, an upper portion portion of the internal diameter being wider that a lower portion of the internal diameter, thus configured to enable angular motion of the endodontic file;
      ii. the ring having a cut narrower than the internal diameter to permit easy insertion of the endodontic file and free movement of the file within the ring;
   c. a threaded hole at the other end of the tubular body, the threaded hole configured to screw onto an ultrasonic hand piece, whereby the cut permits the sideways insertion of the file into the ring without disturbing a working length indicator and the ring activates the file upon manual pressure of the file against the ring.

7. The ultrasonic tip of claim 6 wherein the material of the tip comprises stainless steel, titanium or nickel titanium.

8. The ultrasonic tip of claim 6 wherein the cut width slightly exceeds the width of a standard file.

9. The ultrasonic tip of claim 6 wherein the internal diameter of the ring exceeds the width of a standard file.

10. The ultrasonic tip of claim 6 having the cut and internal ring diameter sized to accommodate other endodontic instruments.

11. The ultrasonic tip of claim 10, wherein the ring is sized to accommodate explorers, scalps, endodontic burs, spoon excavators and Gates Glidden drills.

* * * * *